(12) United States Patent
Shah

(10) Patent No.: US 9,033,959 B2
(45) Date of Patent: May 19, 2015

(54) SKIN GRAFT APPLICATOR

(75) Inventor: Bharat Shah, Springfield, MO (US)

(73) Assignee: Mercy Health System, Inc., Chesterfield, MO (US)

( * ) Notice: Subject to any disclaimer, the term of this patent is extended or adjusted under 35 U.S.C. 154(b) by 828 days.

(21) Appl. No.: 13/031,101

(22) Filed: Feb. 18, 2011

(65) Prior Publication Data

US 2012/0215206 A1  Aug. 23, 2012

(51) Int. Cl.
*A61B 17/00* (2006.01)
*A61B 17/322* (2006.01)

(52) U.S. Cl.
CPC ..... *A61B 17/322* (2013.01); *A61B 2017/00424* (2013.01)

(58) Field of Classification Search
CPC ........... A47L 23/04; A47L 25/00; A47L 1/06; A47L 13/10; A47L 13/00; A43L 21/00; A47K 7/02; A46B 9/04; B25G 1/10; B26B 21/52
USPC ............... 601/135; 427/387; 521/55, 88, 131; 424/78.06
See application file for complete search history.

(56) References Cited

U.S. PATENT DOCUMENTS 5,264,462 A * 11/1993 Hodson et al. ................ 521/88
5,269,037 A * 12/1993 White ..................... 15/104.001
5,290,823 A * 3/1994 Volkert ......................... 521/131
6,887,211 B1 * 5/2005 Sevier et al. .................. 601/135
7,281,288 B1 * 10/2007 McKay ........................ 15/144.2
7,334,286 B2 * 2/2008 Kayser ......................... 15/167.1
7,930,804 B2 * 4/2011 Cornfield ........................ 16/430
7,975,389 B2 * 7/2011 Bozikis et al. .................. 30/527
8,580,239 B2 * 11/2013 Seegert et al. ............. 424/78.06
2006/0251463 A1 * 11/2006 Isaac ............................. 401/197
2007/0209133 A1 * 9/2007 Linzell ......................... 15/209.1
2010/0183814 A1 * 7/2010 Rios et al. ...................... 427/387
2010/0210745 A1 * 8/2010 McDaniel et al. .............. 521/55

FOREIGN PATENT DOCUMENTS

EP            0375579 B1 *  7/1993   .......... B05C 17/0217

OTHER PUBLICATIONS

"Polymeric Foams and Foam Technology" Daniel Klempner, Vahid Sendijarevic, Roza Mikhaïlovna Aseeva, Hanser Verlag, 2004.*
Pointing utensil for therapeutic or medical use EP 0375579 B1 Testelin, Gerard Marie European Patent Office EnglishTranslation.*
Pointing utensil for therapeutic or medical use EP 0375579 B1 EnglishTranslation. Jul. 1993.*

* cited by examiner

*Primary Examiner* — William Thomson
*Assistant Examiner* — Victor Shapiro
(74) *Attorney, Agent, or Firm* — Polsinelli PC; Michael Williamson

(57) ABSTRACT

A skin graft applicator with a handle member and a roller member is described for use in applying a skin graft to a patient. The skin graft applicator has a manipulator pad for positioning the skin graft, and a roller member for forcing air and fluid from underneath the skin graft ensuring the proper bond between graft and tissue.

15 Claims, 4 Drawing Sheets

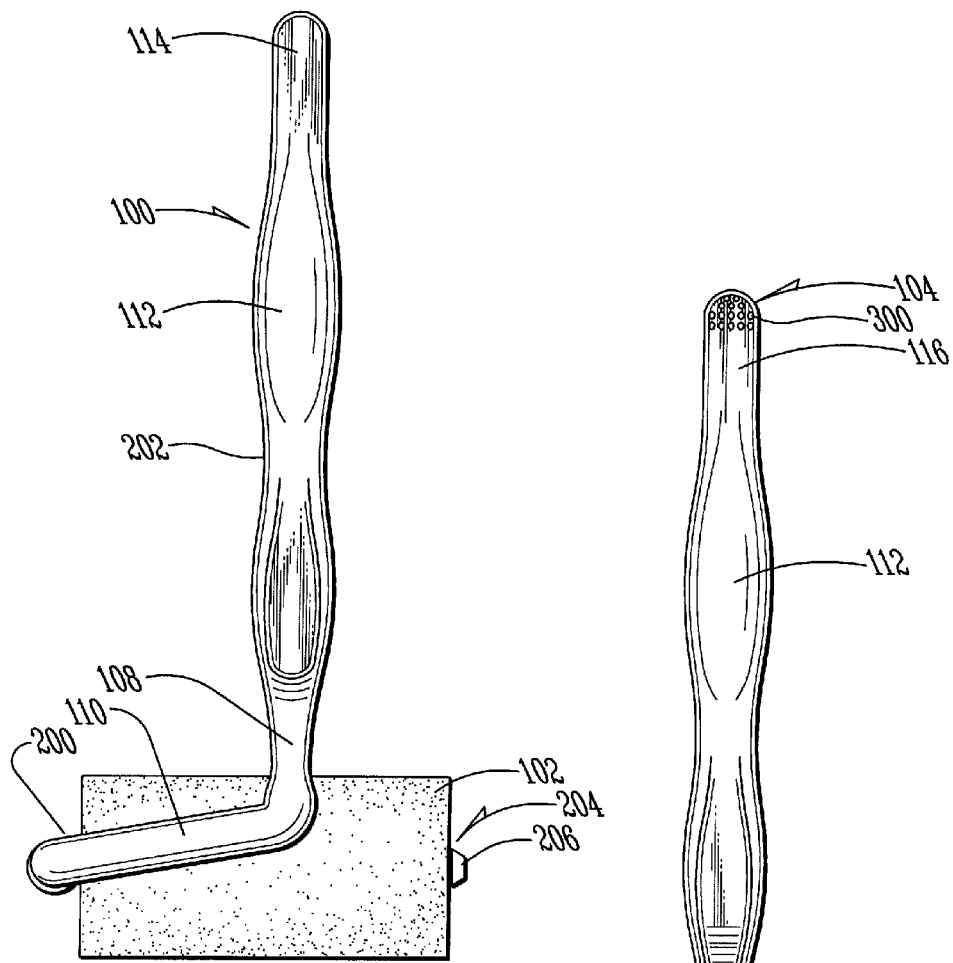
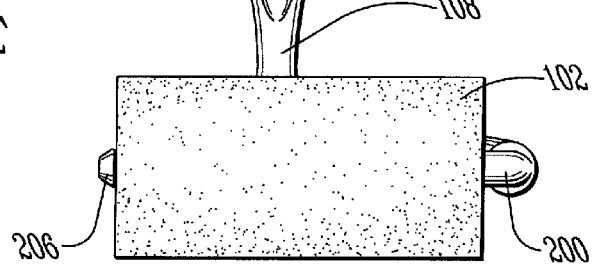

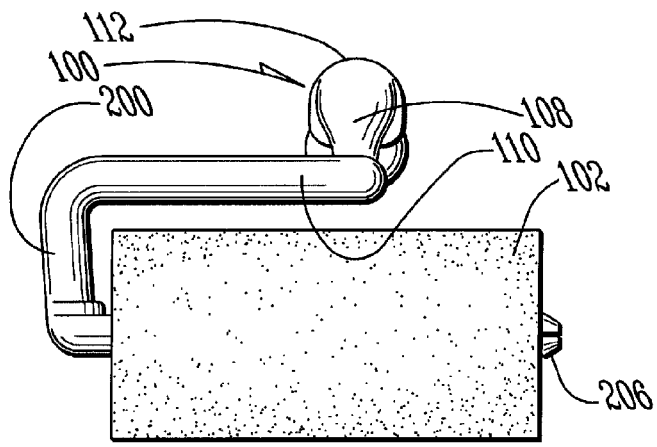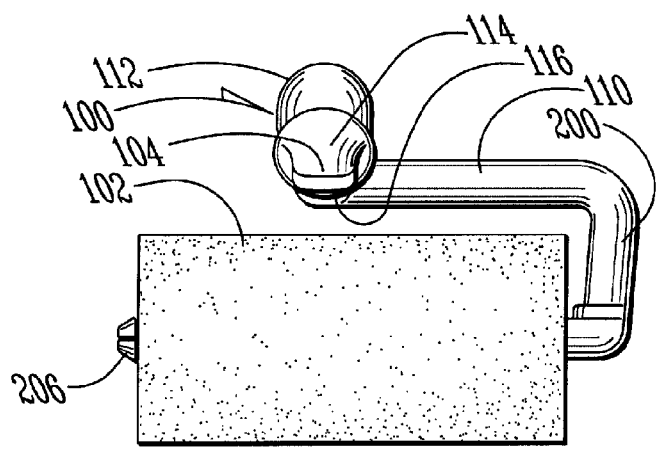

SKIN GRAFT APPLICATOR

BACKGROUND

1. Field of the Invention

The skin graft applicator is in the field of devices and methods for application and positioning of skin grafts during surgical grafting procedures. Skin grafts are typically difficult to reposition once applied to a wound site, as the wound tissue adheres to the skin graft and resists the movement of the graft. Similarly, air bubbles and fluid are often trapped under a skin graft, and are difficult to remove once the graft has been placed on the wound site. It may also be desirable to smooth the skin to prevent wrinkling as much as possible. The applicator described herein provides improved tools for the removal of air bubbles and fluid from underneath the graft and for the positioning and movement of the graft on the wound site.

SUMMARY OF THE INVENTION

The skin graft applicator provides multiple tools for use in repositioning a skin graft in place on a wound site and for removing air bubbles and fluid trapped between the skin graft and the wound site and smoothing the skin graft.

The skin graft applicator comprises a handle member with a manipulator pad; and a roller member rotatably attached to the handle member. In an embodiment of the skin graft applicator described herein, the manipulator pad is disposed adjacent to a first end of the handle member and the roller member is disposed adjacent to a second end of the handle member.

In an embodiment of the skin graft applicator, the manipulator pad comprises a plurality of features extending outwardly from the surface of the handle member. The features in the manipulator pad may comprise hemispheres, or other shapes described with reference to the figures.

In the embodiment of the skin graft applicator described herein, the roller member comprises a cylindrical foam tube. In some embodiments of the skin graft applicator, the foam tube has a foam density between 33 lb/ft$^3$ and 7.5 lb/ft$^3$. In some embodiments of the skin graft applicator, the foam tube has a tensile strength between 14 lb/in$^2$ and 44 lb/in$^2$. In some embodiments of the skin graft applicator, the foam tube is open cell foam, closed cell foam, or semi-open cell foam.

A method of applying a skin graft is described herein comprising the steps of: providing a skin graft applicator having a roller member and a handle member with a manipulator pad; utilizing the manipulator pad to move, the skin graft laterally to the desired position; and rolling the roller member across the skin graft to force air bubbles and fluid to the edges of the skin graft. These steps may be repeated multiple times and in various orders until the desired disposition of the skin graft is achieved.

BRIEF DESCRIPTION OF THE DRAWINGS

FIG. 2 is a top view of an embodiment of the skin graft applicator.

FIG. 3 is a bottom view of an embodiment of the skin graft applicator.

FIG. 6 is a front view of an embodiment of the skin graft applicator.

FIG. 7 is a back view of an embodiment of the skin graft applicator.

DETAILED DESCRIPTION

The skin graft applicator provides an improved device for positioning and repositioning a skin graft on a wound site. Typically when a skin graft is placed on a wound site the exposed wound tissue readily adheres to the interior surface of the skin graft. While the graft may be peeled or similarly removed from the wound site for repositioning, the lateral movement of the skin graft on the wound is resisted by the adherence of the wound and skin graft tissues. Often attempts to reposition the skin graft result in stretching or other deformation of or damage to the skin graft, producing less than optimal results. Similarly, lifting the skin graft away from the wound site to allow repositioning is not desirable.

The skin graft applicator also provides an improved device for removing the air bubbles and fluid trapped between the skin graft and the wound site and smoothing the skin graft out on the wound. When a skin graft is placed on a wound site, air bubbles and fluid are often trapped between the wound tissue and the interior surface of the skin graft. If the bubbles and fluid are allowed to remain between the graft and the wound, the skin graft may be compromised. The skin graft applicator provides an improved tool for removing the air bubbles and fluid.

Figure 1:
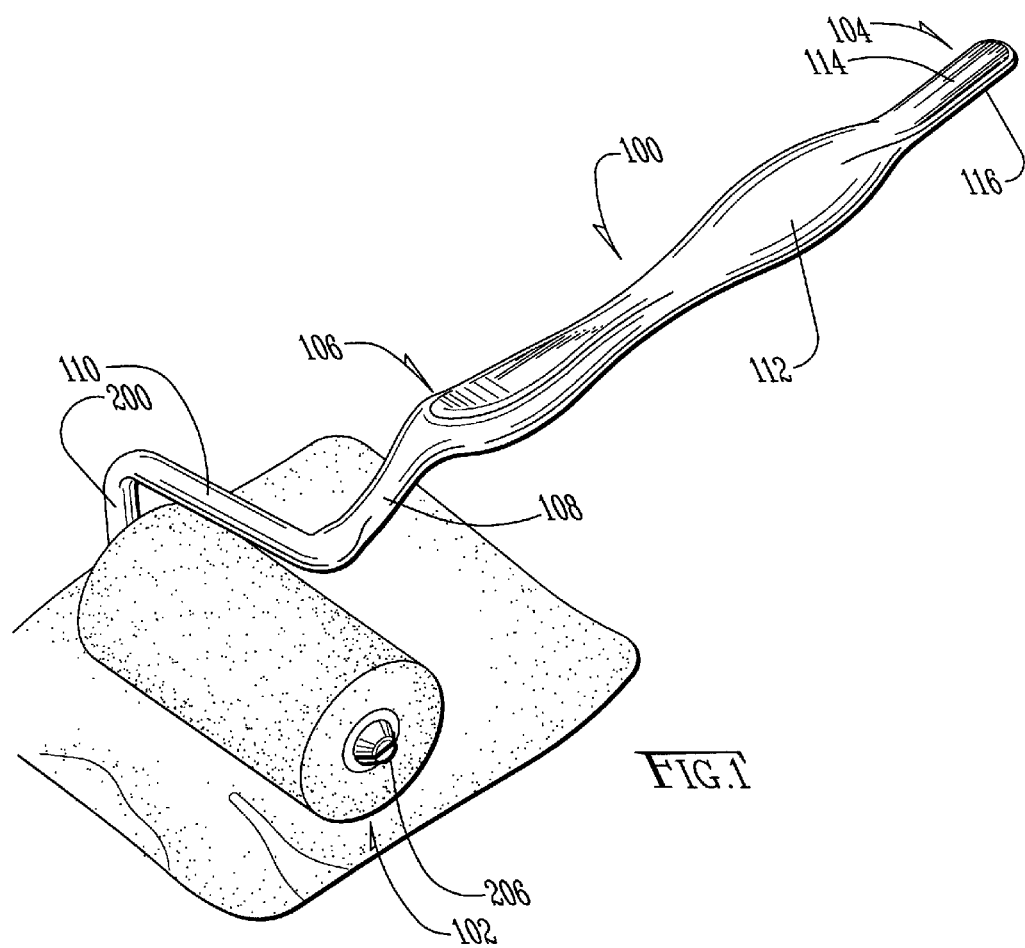
FIG. 1 is a perspective view of an embodiment of the skin graft applicator.

Referring now to FIG. 1, a perspective view of an embodiment of the skin graft applicator is depicted. The applicator comprises a handle member 100 and a roller member 102. The handle member may be formed from plastics, metals, or any other material suitable for machining, casting or otherwise manufacturing into the desired shape. In an embodiment of the applicator the handle is formed from medical grade ISO 10993 biocompatible and sterilizable polymer.

The roller member 102 is utilized to smooth the skin graft over the application site, and to force air bubbles and fluid to the edge of the skin graft and out from under the skin graft by the application of even pressure in a rolling manner across the skin graft. In one embodiment of the applicator, the roller member is formed from open cell foam, such as a medical grade ISO 10993 biocompatible and sterilizable hydrophilic, non-swelling polyurethane foam. In other embodiments of the applicator, the roller member is formed from other foam materials and can be hydrophobic. Additional characteristics of the roller that are preferred are (i) a non-abrasive surface to prevent scratching, tearing or grabbing of graft tissue, (ii) a density firm enough to allow a smooth and constant pressure to be exerted on the graft tissue but soft enough to follow and track the anatomical contours. In some embodiments, the roller may aid in tissue fluid management by absorption, for hydrophilic rollers, or transfer, for hydrophobic rollers, of fluid away from the interstitial space between the parent tissue and the graft tissue to ensure proper bonding of graft tissue.

The handle member 100 is provided with a graft manipulator pad 104 located near a first end of the handle member 100. The manipulator pad 104 is capable of manipulating the graft by pushing or pulling the graft laterally across the wound side. The manipulator pad is provided with surface features described in more detail with reference to a later figure. In the depicted embodiment, pad 104 is a substantially flat extension of the handle member 100, the pad 104 having an upper surface 114 and a lower surface 116. The surface features shown in FIG. 3 are disposed on the lower surface 116 of the pad 104.

Figure 4:
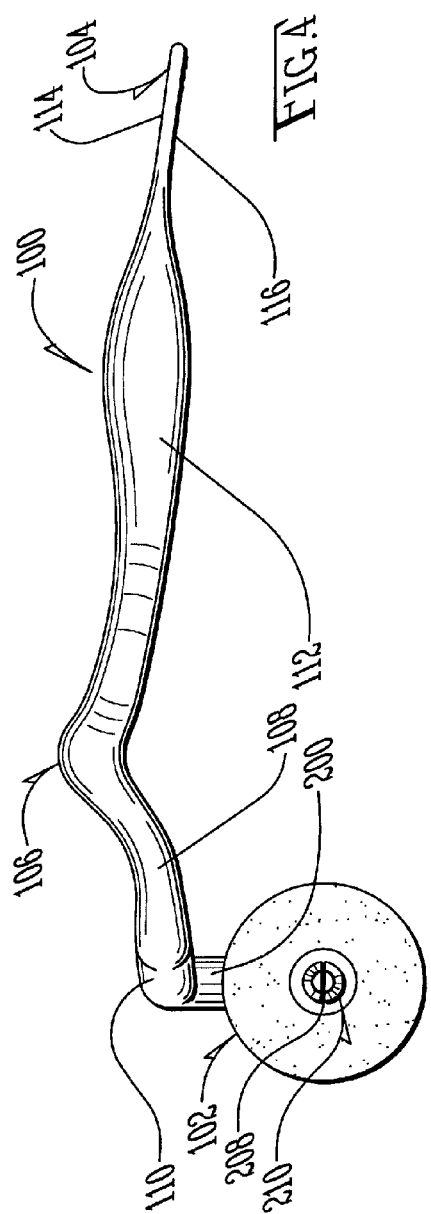
FIG. 4 is a left side view of an embodiment of the skin graft applicator.

The handle member 100 is also provided with a graft manipulator area, or thumb pad, 106 for exerting pressure on the graft to properly position it on the wound site. This area is used as an ergonomic aid to the user to apply force nearer to the normal, or perpendicular to the graft tissue surface. A force exerted normally will reduce lateral forces which tend to move the graft tissue away from the correct position. A grip area 112 is provided in handle member 100 on the section of handle member 100 between the thumb pad 106 and the graft manipulator pad 104. The longitudinal axis of the grip area 112 extends from the graft manipulator pad through the thumb pad 106. In the depicted embodiment, thumb pad 106 comprises a flattened portion of the top surface of the handle member 100 to receive pressure from the hand of a user of the device. As can be seen more clearly in relation to FIGS. 4 and 5, thumb pad 106 extends slightly upwardly from grip area 112. Arcuate section 108 extends from the thumb pad 106. When viewed from the side, as shown in FIG. 4, arcuate section 108 curves downwardly from thumb pad 106 and forward to a forward end above roller member 102. A roller arm 110 extends sideways from the arcuate arm 108 at an angle to the longitudinal axis of handle member 100, as shown in FIG. 2 and FIG. 6. A roller arm extension 200 extends downwardly from the end of roller arm 110. Extension 200 allows roller member 102 to be disposed beneath the end of arcuate section 108. The arcuate section 108 and the orientation of the roller arm 110 and extension 200 dispose roller member 102 substantially beneath the end of arcuate section 108 allowing a user to place downward pressure on roller member 102 from thumb pad 106.

Referring now to FIG. 2, a top view of an embodiment of the skin graft applicator is depicted. The handle member 100 incorporates roller arm 200 for receiving and rotatably supporting roller member 102. The roller arm may be cast or machined as a part of the handle member 100 or separately manufactured and attached to other components of the handle member.

Similar to other roller arms known for various uses, the roller arm extends from the grip area 202 of handle member 100 to the side of roller member 102 and then through a cylindrical opening in roller member 102. The cylindrical opening extends along the rotational axis of the roller member 102. The end 204 of roller arm 200 is provided with a means of retaining roller member 102 on the roller arm 200 during use.

In the embodiment shown in the figures, the end 204 of roller arm 200 is provided with a retaining flange 206 incorporated into the roller arm 200. The arm 200 may also have a transverse slit 208 and retaining ring 210, shown more clearly with reference to a later figure. The retaining flange 206 may be compressed along the length of slit 208, thus allowing retaining ring 210 to be slid over the retaining flange 206, at which time the flange 206 is released and engages the retaining ring 210.

Retaining ring 210 extends axially away from roller arm 200 a sufficient distance to overlap and retain roller member 102 on roller arm 200. In some embodiments, retaining ring 210 may extend cylindrically along the roller arm 200 inside roller member 102 to provide support to the roller member 102 and to maintain it at the appropriate spacing from roller arm 200.

Referring now to FIG. 3, a bottom plan view of an embodiment of the skin graft applicator is depicted. Graft manipulator pad 104 is disposed on the end of handle member 100 opposite to the roller arm 200. The pad 104 provides a user a means of gripping and pulling or pushing the skin graft in a lateral direction on the wound site. In the embodiment shown in the figures, the pad 104 comprises a pattern of features 300 extending outwardly from the surface of handle member 102 adjacent to the end thereof. The pattern of the features 300 may be uniform or random and is not limiting of the manipulator pad 104.

The features 300 may be a variety of shapes extending outwardly from the surface of handle member 100. The shapes may be of various shapes, including, but not limited to hemispherical, semispherical, or polyhedron shapes, or asymmetric shapes such as ridges, hooks, or random shapes. The features 300 provide a means of exerting force on the skin graft by contact and lateral pulling or pushing of the handle member 100. Any shape that grabs the graft tissue without damaging it may be utilized.

In the embodiment depicted in the figures, features 300 are formed as a part of handle member 100. In other embodiments of the skin graft applicator, the pad 104 or features 300 may be separately manufactured and then applied to handle member 100 by gluing, welding or other means of permanently attachment.

During use, the manipulator pad 104 is placed against the skin graft with a substantial part of the surface of pad 104 and features 300 in contact with the skin graft. The handle member 100 is then pulled or pushed laterally to exert force on the skin graft and adjust its position as desired.

Referring now to FIG. 4, a left side view of an embodiment of the skin graft applicator is depicted. The ergonomic handle naturally reduces fatigue and allows the even application of downward force on the face of the roller 102 that is in contact with the graft tissue.

The embodiment of the applicator shown in FIG. 4 comprises a handle member 100 that has an optional taper to a thin flat area near manipulator pad 104. The thin area of handle member 100 provides some flexibility to handle 100 when pad 104 is pressed against a skin graft and allows the user to apply force more efficiently to the skin graft. FIG. 4 also shows the slit 208 and retaining ring 210.

Figure 5:
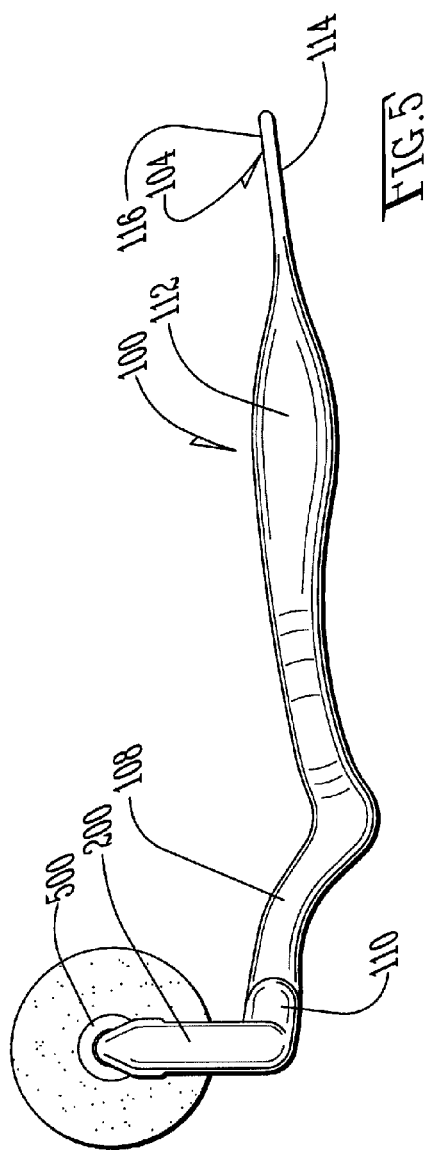
FIG. 5 is a right side view of an embodiment of the skin graft applicator.

Referring now to FIG. 5, a right side view of an embodiment of the skin graft applicator is depicted. A second retaining ring 500 is depicted between roller member 102 and roller arm 200. Like retaining ring 210, ring 500 maintains roller member 102 at the appropriate position laterally on roller arm 200. The ring 500 may optionally extend inside roller member 102 along roller arm 200 to maintain the appropriate distance axial distance between the two components, and to ease the rotation of roller member 102 around roller arm 200.

Referring now to FIGS. 6 and 7, a front and rear view of the skin graft applicator is depicted.

The skin graft applicator is utilized to complete the application of a skin graft. Once the skin graft is disposed on the wound site the roller member and manipulator pad are utilized as necessary to dispose the skin graft in the final desired position and configuration. The manipulator pad may be utilized to move the skin graft laterally on the wound site and then the roller member may be utilized to force air and fluid from under the skin graft and smooth it out on the wound site. Bach step may be repeated separately a plurality of times, and in whatever order is necessary to achieve the desired result.

What is claimed is:
1. A skin graft applicator comprising:
a handle member comprising a manipulator pad disposed at a first end of the handle member, a grip area adjacent to the manipulator pad, a thumb pad adjacent to the grip area, an arcuate section attached to the thumb pad and a roller arm extending from the arcuate section;

a roller member rotatably attached to the roller arm;

wherein the roller arm extends substantially perpendicular to the longitudinal axis of the grip area; and wherein the roller arm positions the rotational axis of the roller member apart from and perpendicular to the longitudinal axis of the grip area.

2. The skin graft applicator of claim 1 wherein the thumb pad extends at an angle upwardly from the grip area and the arcuate section is curved and extends downwardly and forward from the thumb pad to a forward end of the arcuate section; and wherein the roller arm disposes the roller member on the opposite side of the handle member from the thumb pad.

3. The skin graft applicator of claim 2 wherein the manipulator pad further comprises a plurality of features extending outwardly from the surface of the handle member.

4. The skin graft applicator of claim 3 wherein the features comprise hemispheres.

5. The skin graft applicator of claim 3 wherein the roller member comprises a cylindrical foam tube.

6. The skin graft applicator of claim 5 wherein the foam tube has a foam density between 3.5 lb/ft$^3$ and 7.5 lb/ft$^3$.

7. The skin graft applicator of claim 5 wherein the foam tube has a tensile strength of between 14 lb/in$^2$ and 44 lb/in$^2$.

8. The skin graft applicator of claim 5 wherein the foam tube is open cell foam.

9. A method of using the skin graft applicator of claim 1 to apply a skin graft comprising the steps of:

utilizing the manipulator pad to move the skin graft laterally to a desired position; and rolling the roller member across the skin graft with the grip area substantially parallel to the skin graft while exerting a force on the thumb pad in a direction perpendicular to the surface of the skin graft to force air bubbles to the edges of the skin graft without substantial lateral movement of the skin graft.

10. The method of claim 9 wherein the manipulator pad comprises a plurality of features extending outwardly from the surface of the handle member.

11. The method of claim 10 wherein the features are hemispheres.

12. The method of claim 10 wherein the roller member comprises an open-cell foam cylindrical tube.

13. The method of claim 12 Wherein the roller member has a foam density between 3.5 lb/ft$^3$ and 7.5 lb/ft$^3$.

14. The method of claim 12 wherein the roller member has a tensile strength of between 14 lb/in$^2$ and 44 lb/in$^2$.

15. The skin graft applicator of claim 2 wherein the manipulator pad comprises a flat extension having an upper surface and a lower surface, and a plurality of surface features extending from the lower surface of the manipulator pad for manipulating a skin graft.

\* \* \* \* \*